United States Patent
O'Rear et al.

(10) Patent No.: US 6,392,109 B1
(45) Date of Patent: May 21, 2002

(54) SYNTHESIS OF ALKYBENZENES AND SYNLUBES FROM FISCHER-TROPSCH PRODUCTS

(75) Inventors: Dennis J. O'Rear, Petaluma; William L. Schinski, San Rafael, both of CA (US)

(73) Assignee: Chevron U.S.A. Inc., San Ramon, CA (US)

(*) Notice: Subject to any disclaimer, the term of this patent is extended or adjusted under 35 U.S.C. 154(b) by 0 days.

(21) Appl. No.: 09/514,958

(22) Filed: Feb. 29, 2000

(51) Int. Cl.[7] ................................. C07C 5/00
(52) U.S. Cl. ................. 585/323; 585/323; 585/319; 585/317
(58) Field of Search ................. 585/319, 323, 585/317

(56) References Cited

U.S. PATENT DOCUMENTS

| | | | |
|---|---|---|---|
| 2,662,090 A | 12/1953 | Scharmann | 518/718 |
| 2,686,195 A | 8/1954 | McAdams et al. | 518/718 |
| 2,735,862 A | 2/1956 | Buchmann et al. | 518/715 |
| 2,850,515 A | 9/1958 | Riblett | 518/715 |
| 2,882,244 A | 4/1959 | Milton | 423/718 |
| 3,130,007 A | 4/1964 | Breck et al. | 423/711 |
| 3,216,789 A | 11/1965 | Breck et al. | 423/718 |
| 3,308,069 A | 3/1967 | Wadlinger et al. | 502/62 |
| 3,415,736 A | 12/1968 | Ciric | 208/111.15 |
| 3,445,541 A | 5/1969 | Heckelsberg et al. | 585/630 |
| 3,546,102 A | 12/1970 | Bertolacini | 208/138 |
| 3,574,092 A | 4/1971 | Mitsche | 208/139 |

(List continued on next page.)

FOREIGN PATENT DOCUMENTS

| | | |
|---|---|---|
| EP | 353915 A2 | 2/1990 |
| EP | 498182 A1 | 8/1992 |
| EP | 0558148 A1 | 1/1993 |
| EP | 0560437 A1 | 9/1993 |
| EP | 0731072 A1 | 9/1996 |

(List continued on next page.)

OTHER PUBLICATIONS

Briant, J., "Structure/property relationships of viscosity and flow at low temperature" *Rheological Properties of Lubricants*, Chapter 7, 1989, Gulf Publishing Co., Paris, Edition Technip, pp. 123–163.

Khan, M.K.Z., et al., "The Synthesis of Light Hydrocarbons from CO and $H_2$ Mixtures over Selected Metal Catalysts," *ACS 173rd Symposium Series 64, Fuel Division*, New Orleans, Mar. 1977 pp 138–147.

(List continued on next page.)

*Primary Examiner*—Thuan D. Dang
(74) *Attorney, Agent, or Firm*—Burns, Doane, Swecker & Mathis, L.L.P.; Melissa M. Hayworth

(57) ABSTRACT

An integrated process for producing alkylbenzenes, sulfonated alkylbenzenes and/or alkylcyclohexanes from syngas is disclosed. The process involves subjecting syngas to Fischer-Tropsch conditions. Fractions rich in $C_{6-8}$ and $C_{18-26}$ hydrocarbons are isolated from the resulting product stream. The $C_{6-8}$ fraction is subjected to catalytic reforming conditions to form aromatics. The $C_{18-26}$ fraction may include sufficient olefins for use in an alkylation reaction with the aromatics. Optionally, the fraction may be subjected to dehydrogenation conditions to provide additional olefins. The resulting olefins are reacted with the aromatics in an alkylation reaction to yield alkylbenzenes. Unconverted olefins, paraffins, and aromatics can be obtained from the product stream via fractional distillation and recycled to form additional products. The alkylbenzenes can be hydrogenated to yield alkylcyclohexanes, which are useful as synlubes or as components in lube oil compositions. Alternatively, the alkylbenzenes can be sulfonated, and the resulting sulfonated alkylbenzenes used, for example, as detergents and/or dispersants.

28 Claims, 1 Drawing Sheet

U.S. PATENT DOCUMENTS

| | | | |
|---|---|---|---|
| 3,679,575 A | 7/1972 | Bertolacini | 208/65 |
| 3,692,470 A | 9/1972 | Ciric | 423/706 |
| 3,709,979 A | 1/1973 | Chu | 423/700 |
| 3,832,449 A | 8/1974 | Rosinski et al. | 423/705 |
| 3,856,876 A | 12/1974 | Burnett | 585/708 |
| RE28,341 E | 2/1975 | Wadlinger et al. | 208/120 |
| 3,972,983 A | 8/1976 | Ciric | 423/705 |
| 4,016,245 A | 4/1977 | Plank et al. | 423/708 |
| 4,018,711 A | 4/1977 | Bertolacini | 502/66 |
| 4,039,302 A | 8/1977 | Khera | 518/712 |
| 4,042,614 A | 8/1977 | Vannice et al. | 518/715 |
| 4,076,842 A | 2/1978 | Plank et al. | 423/704 |
| 4,077,995 A | 3/1978 | Khera | 518/715 |
| 4,088,671 A | 5/1978 | Kobylinski | 518/715 |
| 4,104,320 A | 8/1978 | Bernard et al. | 585/419 |
| RE29,948 E | 3/1979 | Dwyer et al. | 208/110 |
| 4,148,833 A | 4/1979 | Antos | 585/434 |
| 4,151,190 A | 4/1979 | Murchison et al. | 518/714 |
| 4,171,320 A | 10/1979 | Vannice et al. | 518/715 |
| 4,241,036 A | 12/1980 | Flanigen et al. | 502/62 |
| 4,310,440 A | 1/1982 | Wilson et al. | 502/208 |
| 4,347,121 A | 8/1982 | Mayer et al. | 208/58 |
| 4,347,394 A | 8/1982 | Detz et al. | 585/419 |
| 4,370,224 A | 1/1983 | Eberly, Jr. et al. | 208/139 |
| 4,417,083 A | 11/1983 | Bernard et al. | 585/419 |
| 4,420,649 A | 12/1983 | Antos | 585/434 |
| 4,434,311 A | 2/1984 | Buss et al. | 585/444 |
| 4,440,871 A | 4/1984 | Lok et al. | 502/214 |
| 4,447,316 A | 5/1984 | Buss | 208/138 |
| 4,456,527 A | 6/1984 | Buss et al. | 208/89 |
| 4,476,344 A | 10/1984 | Kimble | 585/661 |
| 4,482,646 A | 11/1984 | Eastman et al. | 508/324 |
| 4,500,651 A | 2/1985 | Lok et al. | 502/208 |
| 4,507,517 A | 3/1985 | Devries et al. | 585/415 |
| 4,530,824 A | 7/1985 | Arika et al. | 423/328 |
| 4,534,853 A | 8/1985 | Long et al. | 208/120 |
| 4,544,539 A | 10/1985 | Wortel | 423/328 |
| 4,544,674 A | 10/1985 | Fiato et al. | 518/717 |
| 4,552,731 A | 11/1985 | Vaughan | 423/118 |
| 4,554,143 A | 11/1985 | Messina et al. | 423/306 |
| 4,556,477 A | 12/1985 | Dwyer | 208/111 |
| 4,567,029 A | 1/1986 | Wilson et al. | 423/300 |
| 4,579,986 A | 4/1986 | Sie | 585/324 |
| 4,585,747 A | 4/1986 | Valyocsik | 502/62 |
| 4,599,474 A | 7/1986 | Devries et al. | 585/415 |
| 4,634,518 A | 1/1987 | Buss et al. | 208/138 |
| 4,681,865 A | 7/1987 | Katsuno | 502/74 |
| 4,686,093 A | 8/1987 | Flanigen et al. | 423/306 |
| 4,686,316 A | 8/1987 | Morrison | 585/708 |
| 4,704,487 A | 11/1987 | Devries et al. | 585/417 |
| 4,704,493 A | 11/1987 | Devries | 585/415 |
| 4,709,108 A | 11/1987 | Devries et al. | 585/415 |
| 4,734,537 A | 3/1988 | Devries et al. | 585/415 |
| 4,751,342 A | 6/1988 | Kimble | 585/622 |
| 4,761,512 A | 8/1988 | Katsuno et al. | 585/417 |
| 4,777,319 A | 10/1988 | Kung et al. | 585/624 |
| 4,778,942 A | 10/1988 | Vora et al. | 585/655 |
| 4,798,911 A | 1/1989 | Lentz et al. | 568/747 |
| 4,810,357 A | 3/1989 | Chester et al. | 208/78 |
| 4,814,533 A | 3/1989 | Devries et al. | 585/407 |
| 4,814,534 A | 3/1989 | Devries et al. | 585/407 |
| 4,814,538 A | 3/1989 | Devries et al. | 585/500 |
| 4,827,066 A | 5/1989 | Herber et al. | 585/319 |
| 4,827,072 A | 5/1989 | Imai et al. | 585/443 |
| 4,827,667 A | 5/1989 | Jarvis | 49/280 |
| 4,834,977 A | 5/1989 | Kohama et al. | 424/405 |
| 4,859,422 A | 8/1989 | Qureshi et al. | 422/81 |
| 4,859,442 A | 8/1989 | Zones et al. | 423/277 |
| 4,861,743 A | 8/1989 | Flank et al. | 502/214 |
| 4,880,764 A | 11/1989 | Imai et al. | 502/320 |
| 4,897,253 A | 1/1990 | Jenkins | 423/651 |
| 4,910,006 A | 3/1990 | Zones et al. | 423/328 |
| 4,929,792 A | 5/1990 | Dessau | 585/661 |
| 4,941,981 A | 7/1990 | Perricone et al. | 252/8.51 |
| 4,956,517 A | 9/1990 | Johnson et al. | 585/660 |
| 4,963,337 A | 10/1990 | Zones | 423/277 |
| 4,973,779 A | 11/1990 | Imai et al. | 585/444 |
| 4,973,785 A | 11/1990 | Lok et al. | 585/481 |
| 4,982,047 A | 1/1991 | Barri et al. | 585/660 |
| 5,012,027 A | 4/1991 | Abrevaya et al. | 585/443 |
| 5,053,373 A | 10/1991 | Zones | 502/64 |
| 5,073,652 A | 12/1991 | Katsuno et al. | 585/419 |
| 5,091,351 A | 2/1992 | Murakawa et al. | 502/66 |
| 5,096,883 A | 3/1992 | Mercer et al. | 507/103 |
| 5,106,801 A | 4/1992 | Zones et al. | 502/64 |
| 5,143,886 A | 9/1992 | Iezzi et al. | 502/242 |
| 5,158,665 A | 10/1992 | Miller | 208/46 |
| 5,189,012 A | 2/1993 | Patel et al. | 507/103 |
| 5,200,101 A | 4/1993 | Hsu et al. | 252/47.5 |
| 5,200,377 A | 4/1993 | Zones et al. | 502/62 |
| 5,202,014 A | 4/1993 | Zones et al. | 208/46 |
| 5,254,514 A | 10/1993 | Nakagawa | 502/62 |
| 5,308,822 A | 5/1994 | Iezzi et al. | 502/243 |
| 5,316,753 A | 5/1994 | Nakagawa | 423/706 |
| 5,321,192 A | 6/1994 | Cottrell et al. | 585/659 |
| 5,348,982 A | 9/1994 | Herbolzheimer et al. | 518/700 |
| 5,354,933 A | 10/1994 | Ohashi et al. | 585/419 |
| 5,430,220 A | 7/1995 | Khare et al. | 585/660 |
| 5,437,855 A | 8/1995 | Valyocsik | 423/706 |
| 5,491,119 A | 2/1996 | Verduijn | 502/74 |
| 5,514,362 A | 5/1996 | Miller | 423/702 |
| 5,558,851 A | 9/1996 | Miller | 423/702 |
| 5,559,068 A | 9/1996 | Chen et al. | 502/213 |
| 5,563,314 A | 10/1996 | Agaskar et al. | 585/654 |
| 5,580,540 A | 12/1996 | Nakagawa | 423/718 |
| 5,591,421 A | 1/1997 | Zones | 423/706 |
| 5,624,657 A | 4/1997 | Vaughan | 423/700 |
| 5,633,421 A | 5/1997 | Iezzi et al. | 585/660 |
| 5,898,023 A | 4/1999 | Francisco et al. | 508/236 |
| 5,905,180 A | 5/1999 | Yokoyama et al. | 585/658 |
| 5,939,044 A | 8/1999 | Nakagawa et al. | 423/706 |
| 5,972,203 A | 10/1999 | Smith et al. | 208/113 |

FOREIGN PATENT DOCUMENTS

| | | |
|---|---|---|
| GB | 669313 | 4/1952 |
| GB | 1117568 | 6/1968 |
| GB | 2050859 A | 1/1981 |
| WO | WO01/02325 A1 | 1/2001 |
| WO | WO01/05733 A1 | 1/2001 |

OTHER PUBLICATIONS

Maleville, X, et al., "Oxidation of Mineral Base Oils of Petroleum Origin: The Relationship Between Chemical Composition, Thickening, and Composition of Degradation Products," *Lubrication Science*, 9–1, Nov. 1996, Leaf Coppin Publishing Ltd., Deal, England, pp. 3–60.

Mirozopeva, M.A., et al., *Naftekhimiya*, vol. 28, No. 6, 188, pp. 831–837, Russian Article.

Nakamura, M., et al., "Fischer–Tropsch Synthesis with Iron–Cobalt Alloy," *Studies in Surface Science and Catalysis 7A, New Horizons in Catalysis*, Proceedings of the 7$^{th}$ International Congress on Catalysis, Tokyo, Jun. 3 thru Jul. 4, 1980, Elsevier Scientific Publishing Company, Amsterdam, 1981, pp. 432–446.

Xu, L., et al., "Don't rule out iron catalysts for Fischer–Tropsch synthesis," *Chemtech*, Jan. 1998, published by American Chemical Society, pp. 47–53.

Amelse, J.A., et al., "Iron Alloy Fischer–Tropsch Catalysts, III. Conversion Dependence of Selectivity and Water–Gas Shift," *Journal of Catalysis*, 72,(1981),pp. 95–110.

Bloch, Herman S., "New Route to Linear Alkylbenzenes," *detergent age*, Jan. 1967, pp. 34–35 & p. 105.

Broughton, "Adsorptive Separation (Liquids)," *Kirk–Othmer Encyclopedia of Chemical Technology*, vol. 1 Third Edition, NY, John Wiley & Son 1978, pp. 563–581.

Courty, P. et al., (french article) *C.R. Acad. Sci. Paris*, May 28, 1969, p. 268.

Deckwer, W., et al., "Modeling the Fischer–Tropsch Synthesis in the Slurry Phase,"*Ind. Eng. Chem. Process Des. Dev.*, v21, No. 2, 1982, pp. 231–241.

*Gmelins Handbuch Der Anorganische Chemie, Cadmium*, 8 Auflage, 33, 1959 p. 59.

Hu, Y., "Unconventional Olefin Processes", *Hydrocarbon Processing*, May 1983, pp. 88–96.

Kitzelmann, D., et al., "Zur selektiven Hydrierung von Kohlenmonoxid zu $C_2$–bis $C_4$–Olefinen," *Chem. Ing. Tech.*, 49 1977) No. 6, pp. 463–468.

Kölbel, H., et al., "The Fischer–Tropsch Synthesis in the Liquid Phase", *Catal. Rev. Sci. Eng.*, v 21(n), 1980, pp. 225–274.

Little, D.M. *Catalytic Reforming*, Penn Well Books, (Table of Contents), 1985.

Lo, Cary et al., "Mössbauer and Magnetic Studies of Bifunctional Medium–Pore Zeolite–Iron Catalysts Used in Synthesis Gas Conversion," *American Chemical Society, Advances in Chemistry Series 194*, 1981, pp. 573–588.

Meyers, R., *Handbook of Petroleum Refining Process*, NY, McGraw–Hill, (Table of Contents),1986.

"New Japanese Processes Promise Cheaper Styrene & Xylenes," *Petroleum & Petro–chemical International*, Dec. 1972, vol. 12, No. 12., pp 64–68.

Ramachandran, P., et al. "Bubble Column Slurry Reactor," *Three–Phase Catalytic Reactors*, Chapter 10, Gordon & Broch Science Publishers, 1983, pp. 308–332.

Schultz, R.C. et al, "Lab Production, Second World Conference on Detergents, Looking Towards the 90's," Montreux, Switzerland, Oct. 5 through 19, 1986, pp. 260–267.

Shah, Y.T., et al., "Design Parameters Estimations for Bubble Column Reactors," *AICHE Journal*, vol. 28, No. 3, May 1982, pp. 353–379.

Stanfield, R.M., et al., "Mössbauer Spectroscopy of Supported Fe–Co Alloy Catalysts for Fischer–Tropsch Synthesis," *Journal of Catalysis*, 1981, No. 72(1), pp. 37–50.

Vora, B., "Production of Detergent Olefins and Linear Alkylbenzenes," *Chemical & Industry*, 1990, pp. 187–194.

Woude, F., et al., "Mössbauer Effect in Iron and Dilute Iron Based Alloys," *Physics Reports* (*Sect. C of Physics Letters*), North–Holland Publishing Co., 12 No. 5, 1974, pp. 335–374.

SYNTHESIS OF ALKYBENZENES AND SYNLUBES FROM FISCHER-TROPSCH PRODUCTS

BACKGROUND OF THE INVENTION

There is a large demand for alkylbenzenes and synthetic lubricants (synlubes). Alkylbenzenes are often used as detergents in a variety of applications, for example, as lubricant oils. The preferred alkylbenzenes have linear (as opposed to branched) alkyl groups, and are referred to as linear alkylbenzenes. Linear alkylbenzenes are preferred over branched alkylbenzenes because of their relatively high rate of biodegradability.

Currently, these products are prepared by alkylating normal alpha olefins (NAOs), or isomerized olefins derived from normal alpha olefins, with benzene or toluene. The NAOs are typically made from ethylene, which is a relatively expensive raw material. Accordingly, the cost of the alkylbenzenes and synlubes is relatively high. NAOs can also be prepared by wax cracking and by modified ethylene oligomerization processes.

Linear alkylbenzenes can also be prepared from high purity unbranched paraffins by dehydrogenating the paraffins to form olefins, and then alkylating aromatic rings with the olefins. However, this approach is limited by the relatively high cost of the paraffinic starting material and the limited supply of high quality unbranched paraffins. If the paraffins are not extremely pure, but rather, include isoparaffins or naphthenes, the catalysts tend to foul and the products tend not to perform adequately.

One type of synthetic lubricant is derived from 1-decene that has been trimerized and hydrogenated to form a T-shaped $C_{30}$ isoparaffin. The particular shape of the molecule provides it with a relatively high viscosity index and low pour point, which is desirable for synthetic lubricants. However, the decene trimer is not unique. Many alkylcyclohexanes also have relatively high viscosity indexes (VI's) and low pour points (Briant et al., "Rheological properties of lubricants", Editions Tecnip (Chapter 7 (1989).

It would be desirable to provide additional methods for forming alkylbenzenes and alkylcyclohexanes. The present invention provides such methods.

SUMMARY OF THE INVENTION

In its broadest aspect, the present invention is directed to an integrated process for preparing alkylbenzenes, sulfonated alkylbenzenes and/or alkylcyclohexanes from syngas. In the first step, syngas is reacted under Fischer-Tropsch conditions to form one or more product streams that include $C_{6-8}$ and $C_{18-26}$ fractions. These fractions can be isolated, for example, via conventional fractional distillation. Both fractions are optionally but preferably treated, for example, by hydrotreating or extraction, to remove oxygenates and other by-products of the Fischer-Tropsch synthesis.

The $C_{6-8}$ fraction can be converted to aromatics via catalytic reforming chemistry, preferably using the AROMAX® Process. The $C_{6-8}$ fraction is ideal for use in the AROMAX® Process, because it tends to have low levels of sulfur, a known poison for the catalyst used in the AROMAX® Process.

The $C_{18-26}$ fraction tends to be highly linear, and also has low levels of impurities known to adversely affect processes for alkylating aromatics with olefins. Depending on the particular Fischer-Tropsch conditions, the fraction may include sufficient olefins and alcohols such that it can be directly reacted with aromatics to form alkylbenzenes. The aromatics and $C_{18-26}$ hydrocarbons used to form the alkylbenzenes can be derived exclusively from the $C_{6-8}$ and $C_{18-26}$ fractions from the Fischer-Tropsch reaction, or can optionally be combined with aromatics and/or $C_{18-26}$ hydrocarbons from other feedstocks, assuming that the other feedstocks do not include impurities that would have a detrimental effect on the subsequent chemistry.

The paraffinic portion of the $C_{18-26}$ fraction can be dehydrogenated to form olefins and reacted with the aromatics. The alkylbenzenes can be used, for example, as lubricant oils, or can be sulfonated to form detergents.

The alkylbenzenes can be reduced to form alkylcyclohexanes. In one embodiment, the hydrogen produced during the catalytic reforming chemistry can be used to hydrogenate the alkylbenzenes to form the alkylcyclohexanes. The resulting alkylcyclohexanes can be used, for example, as synlubes or as a component in synlube compositions. Preferably, the lubricant compositions, including the alkylbenzenes and/or alkylcyclohexanes, also include conventional lubricant additives.

In one embodiment, the Fischer-Tropsch chemistry is performed in two separate reactors, in order to maximize the relative amounts of $C_{6-8}$ and $C_{18-26}$ fractions. The first reactor can be set up using conditions in which chain growth probabilities are relatively low to moderate, and the product of the reaction includes a relatively high proportion of low molecular ($C_{2-8}$) weight olefins and a relatively low proportion of high molecular weight ($C_{30}+$) waxes. This set of conditions optimizes yields of the $C_{6-8}$ fraction used to form the aromatic rings which are to be alkylated with the $C_{18-26}$ paraffins. Preferred catalysts are iron-containing catalysts.

The second reactor can be set up using conditions in which chain growth probabilities are relatively high, and the product of the reaction includes a relatively low proportion of low molecular ($C_{2-8}$) weight olefins and a relatively high proportion of high molecular weight ($C_{30}+$) waxes. Preferred catalysts are cobalt-containing catalysts. This set of conditions optimizes yields of the $C_{18-26}$ fraction used to alkylate the aromatic rings.

DETAILED DESCRIPTION OF THE INVENTION

Figure 1:
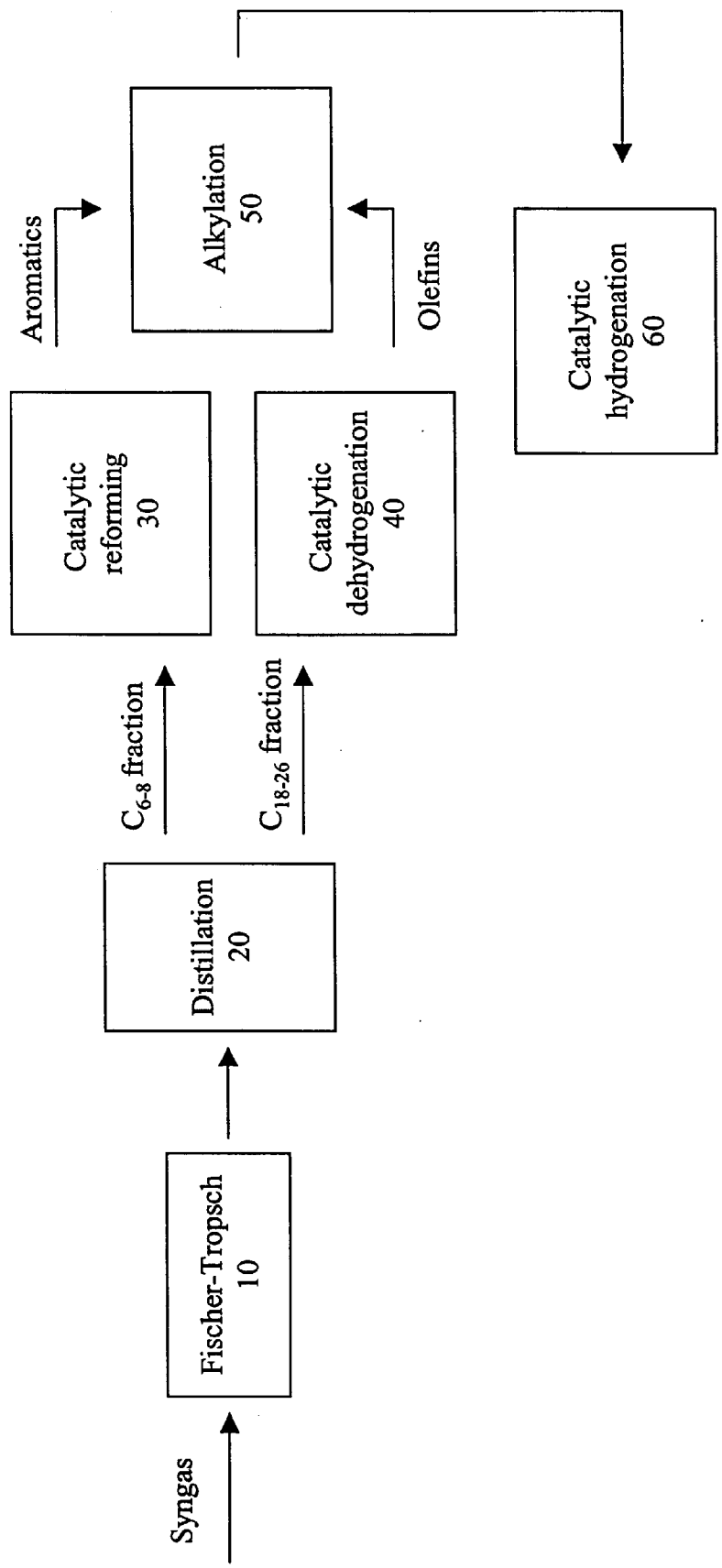
FIG. 1 is a schematic flow diagram representing one embodiment of the invention.

The present invention is directed to an integrated process for producing alkylbenzenes, sulfonated alkylbenzenes and/ or alkylcyclohexanes from syngas. As used herein, the term "integrated process" refers to a process comprising a sequence of steps, some of which may be parallel to other steps in the process, but which are interrelated or somehow dependent upon either earlier or later steps in the total process.

Fischer-Tropsch chemistry is used to convert the syngas to a product stream which includes a $C_{6-8}$ fraction and a $C_{18-26}$ fraction. The Fischer-Tropsch chemistry provides products which are highly linear and which include low levels of sulfur. The $C_{6-8}$ fraction is subjected to catalytic reforming conditions for form $C_{6-8}$ aromatics. The $C_{18-26}$ fraction is dehydrogenated to form $C_{18-26}$ olefins, which are used to alkylate the $C_{6-8}$ aromatics. The aromatics and $C_{18-26}$ hydrocarbons used to form the alkylbenzenes can be exclusively from the Fischer-Tropsch reaction, or can optionally be combined with aromatics and/or $C_{18-26}$ hydrocarbons from other feedstocks. The resulting alkylbenzenes can be used directly, or can be sulfonated to form sulfonated alkylbenzenes or hydrogenated to form alkylcyclohexanes.

Fischer-Tropsch Chemistry

In Fischer-Tropsch chemistry, syngas is converted to liquid hydrocarbons by contact with a Fischer-Tropsch catalyst under reactive conditions. Depending on the quality of the syngas, it may be desirable to purify the syngas prior to the Fischer-Tropsch reactor to remove carbon dioxide produced during the syngas reaction and any sulfur compounds, if they have not already been removed. This can be accomplished, for example, by contacting the syngas with a mildly alkaline solution (e.g., aqueous potassium carbonate) in a packed column.

Examples of conditions for performing Fischer-Tropsch type reactions are well known to those of skill in the art. Suitable conditions are described, for example, in U.S. Pat. Nos. 4,704,487, 4,507,517, 4,599,474, 4,704,493, 4,709,108, 4,734,537, 4,814,533, 4,814,534 and 4,814,538, the contents of each of which are hereby incorporated by reference in their entirety.

In general, Fischer-Tropsch catalysts contain a Group VIII transition metal on a metal oxide support. The catalysts may also contain a noble metal promoter(s) and/or crystalline molecular sieves. Certain catalysts are known to provide chain growth probabilities that are relatively low to moderate, and the reaction products include a relatively high proportion of low molecular ($C_{2-8}$) weight olefins and a relatively low proportion of high molecular weight ($C_{30}+$) waxes. Certain other catalysts are known to provide relatively high chain growth probabilities, and the reaction products include a relatively low proportion of low molecular ($C_{2-8}$) weight olefins and a relatively high proportion of high molecular weight ($C_{30}+$) waxes. Such catalysts are well known to those of skill in the art and can be readily obtained and/or prepared. The product in the $C_{18-26}$ range may include sufficient olefins and alcohols for use in alkylation reactions with aromatics, depending on the Fischer-Tropsch conditions. For example, Fischer-Tropsch reactions using an iron catalyst and run at a relatively high temperature tend to provide a $C_{18-26}$ fraction that includes a sufficient amount of olefins for the alkylation reaction.

Catalyst Selection

Catalysts with Low Chain Growth Probabilities

In order to provide a product stream from a Fischer-Tropsch reaction including a relatively large $C_{6-8}$ fraction, any catalyst that provides relatively low to moderate chain growth probabilities can be used. Typically, catalysts with an alpha value between about 0.600 and 0.700 provide low chain growth probabilities. Catalysts with an alpha value between about 0.700 and 0.800 provide moderate chain growth probabilities. Preferable catalysts are those which tend to provide high yields (i.e., greater than about 20 and more preferably greater than about 30 percent by weight of the products other than methane) of light ($C_{2-8}$) alpha olefins.

Preferred catalysts are iron-containing catalysts. Iron itself can be used and, when iron oxides are formed, can be reduced with hydrogen back to iron. However, because the presence of iron fines in the product stream is not preferred, and because iron oxides (rust) decrease the surface area of the catalyst available for reaction, other iron-containing catalysts may be preferred. Examples of suitable iron-containing catalysts include those described in U.S. Pat. No. 4,544,674 to Fiato et al. and Xu et al., pp. 47–53, *Chemtech* (January 1998).

In a preferred embodiment, the iron catalysts include at least about 10 to about 60 weight percent iron. More preferably, they include between about 20 to about 60 weight percent iron, and most preferably about 30 to about 50 weight percent iron. These catalysts can be unsupported, but are preferably promoted with a refractory metal oxide ($SiO_2$, $Al_2O_3$, etc.), alkali (K, Na, Rb) and/or Group IB metals (Cu, Ag). These catalysts are usually calcined, but usually are not reduced. Rather, they are brought up to reaction temperature directly in the $CO/H_2$ feed.

Co-precipitated iron-based catalysts, including those containing cobalt, can be used. High levels of cobalt in an iron-cobalt alloy are known to produce enhanced selectivity to olefinic products, as described, for example, in *Stud. Surf. Sci. Catal.* 7, Pt/A, p. 432 (1981).

Examples of co-precipitated iron-cobalt catalysts and/or alloys include those described in U.S. Pat. Nos. 2,850,515, 2,686,195, 2,662,090, and 2,735,862; AICHE 1981 Summer Nat'l Meeting Preprint No. 408, "The Synthesis of Light Hydrocarbons from CO and $H_2$ Mixtures over Selected Metal Catalysts", ACS 173rd Symposium, Fuel Division, New Orleans, March 1977; *J. Catalysis* 1981, No. 72(1), pp. 37–50; Adv. Chem. Ser. 1981, 194, 573–88; Physics Reports (Section C of Physics Letters) 12 No. 5 (1974) pp. 335–374; UK patent application No. 2050859A; *J. Catalysis* 72, 95–110 (1981); Gmelins Handbuch der Anorganische Chemie 8, Auflage (1959), pg. 59; *Hydrocarbon Processing*, May 1983, pp. 88–96; and *Chem. Ing. Tech.* 49 (1977) No. 6, pp. 463–468.

Methods for producing high surface area metal oxides are described, for example, in the French article, "*C. R. Acad. Sc. Paris*", p. 268 (May 28, 1969) by P. Courte and B. Delmon. Metal oxides with a high surface area are prepared by evaporating to dryness aqueous solutions of the corresponding glycolic acid, lactic acid, malic or tartaric acid metal salts. One oxide that was prepared was $CoFe_2O_4$.

Iron-cobalt spinels which contain low levels of cobalt, in an iron/cobalt atomic ratio of 7:1 to 35:1, are converted to Fischer-Tropsch catalysts upon reduction and carbiding (see, for example, U.S. Pat. No. 4,544,674 to Fiato et al.). These catalysts tend to exhibit high activity and selectivity for $C_2$–$C_6$ olefins and low methane production.

The contents of each of the patents and publications referred to above are hereby incorporated by reference.

Catalysts with High Chain Growth Probabilities

In order to provide a product stream from a Fischer-Tropsch reaction including a relatively large $C_{18-26}$ fraction, any catalyst that provides relatively high chain growth probabilities can be used. Preferably, the catalyst used in the second stage is a cobalt-containing catalyst. Ruthenium is also an effective Fischer-Tropsch catalyst, but is more expensive.

One suitable cobalt catalyst that can be used is described in U.S. Pat. No. 4,579,986, as satisfying the relationship:

$$(3+4R) > L/S > (0.3+0.4R),$$

wherein:
L=the total quantity of cobalt present on the catalyst, expressed as mg Co/ml catalyst;
S=the surface area of the catalyst, expressed as $m^2$/ml catalyst; and R=the weight ratio of the quantity of cobalt deposited on the catalyst by kneading to the total quantity of cobalt present on the catalyst.

Other suitable catalysts include those described in U.S. Pat. Nos. 4,077,995, 4,039,302, 4,151,190, 4,088,671, 4,042,614 and 4,171,320. U.S. Pat. No. 4,077,995 discloses a catalyst that includes a sulfided mixture of CoO, $Al_2O_3$ and ZnO. U.S. Pat. No. 4,039,302 discloses a mixture of the oxides of Co, Al, Zn and Mo. U.S. Pat. No. 4,151,190 discloses a metal oxide or sulfide of Mo, W, Re, Ru, Ni or Pt, plus an alkali or alkaline earth metal, with Mo—K on carbon being preferred.

U.S. Pat. No. 4,088,671 discloses minimizing methane production by using a small amount of ruthenium on a cobalt catalyst. Supported ruthenium catalysts suitable for hydrocarbon synthesis via Fischer-Tropsch reactions are disclosed, for example, in U.S. Pat. Nos. 4,042,614 and 4,171,320.

In general, the amount of cobalt present in the catalyst is between about 1 and about 50 weight percent of the total catalyst composition, more preferably between about 10.0 and 25 weight percent.

Preferably, the catalyst contains between about 3 and 60 ppw cobalt, between 0.1 and 100 ppw of at least one of zirconium, titanium or chromium per 100 ppw of support (typically, silica, alumina, or silica-alumina and mixtures thereof).

Catalyst Supports

The type of support used can influence methane production. Suitable metal oxide supports or matrices which can be used to minimize methane production include alumina, titania, silica, magnesium oxide, alkaline earth titanates, alkali titanates, rare earth titanates and mixtures thereof.

Methane production can be decreased using supported ruthenium catalysts. Titania or titania-containing supports provide lower methane production than, for example, silica, alumina or manganese oxide supports. Accordingly, titania and titania-containing supports are preferred.

Typically, the catalysts have a particle size of between 10 and 110 microns, preferably between 20 and 80 microns, more preferably between 25 and 65 microns, and have a density of between 0.25 and 0.9 g/cc, preferably between 0.3 and 0.75 g/cc. The catalysts typically include one or more of the above-mentioned catalytic metals, preferably including iron in the first stage and cobalt in the second stage, on one of the above-mentioned catalyst supports. Preferably, the cobalt-containing catalysts include about 10 to 14 percent cobalt on a low density fluid support, for example, alumina, silica and the like, having a density within the ranges set forth above for the catalyst.

Promoters and Noble Metals

Methane selectivity is also influenced by the choice of promoter. Alkali metal promoters are known for reducing the methane selectivities of iron catalysts. Noble metals, such as ruthenium, supported on inorganic refractory oxide supports, exhibit superior hydrocarbon synthesis characteristics with relatively low methane production. Where a noble metal is used, platinum and palladium are generally preferred. Accordingly, alkali metal promoters and/or noble metals can be included in the catalyst bed of the first stage provided that they do not significantly alter the reaction kinetics from slow chain growth probabilities to fast chain growth probabilities.

The disclosures of each of the patents and articles discussed above are incorporated herein by reference in their entirety.

Operating Conditions

Fischer-Tropsch reactions designed to produce a relatively high proportion of the $C_{6-8}$ fraction are typically conducted at temperatures between about 270° C. and 280° C., at a pressure of between about 1 and 20 ATM, in a slurry reactor or a fluidized bed reactor. Typical synthesis gas linear velocity ranges in the reactor are between about 2 and 40 cm per sec., preferably between about 6 and 10 cm per sec.

The products of the Fischer-Tropsch reaction include methane, $C_{2-5}$ hydrocarbons, $C_6+$ hydrocarbons, water and carbon dioxide, as well as unreacted syngas. Water, methane, $C_{2-5}$ hydrocarbons and carbon dioxide are substantially removed to yield a product stream including mostly $C_6+$ hydrocarbons. The $C_6+$ hydrocarbons are predominantly $C_{6-8}$ hydrocarbons, which tend to be roughly 75% by weight olefins, and 25% by weight paraffins. Optionally, but preferably, the product stream is hydrotreated at this stage to remove any oxygenated products. If desired, the $C_{6-8}$ hydrocarbons can be isolated, for example, via distillation.

Fischer-Tropsch reactions designed to produce a relatively high proportion of the $C_{18-26}$ fraction are typically conducted in either a fixed bed reactor or a slurry reactor, where slurry reactors are preferred. The operating temperature of the fixed bed reactor is between about 200° C. and 225° C., and the operating temperature of the slurry reactor is between about 225° C. and 250° C., with a temperature around 240° C. preferred. Typical synthesis gas linear velocity ranges in the reactor are from about 2 to 40 cm per sec., preferably from about 6 to 10 cm per sec. The pressure is preferably between about 1 and 30 ATM, with pressures between 20 and 30 ATM being particularly preferred. Above about 30 ATM, carbonyls may be formed and, therefore, pressures significantly above 30 ATM are not preferred. Further, the rate of reaction tends to increase with increased pressure, but tends to level off due to hydrodynamic problems at around 30 ATM.

The catalyst space velocities are typically between about 100 and 10,000 cc/g/h, preferably between about 300 and 3,000 cc/g/h, for both stages.

The reaction mixture is preferably cooled to less than 100° C., and liquid products are trapped. Methane is preferably bled off to a syngas generator and recycled. Water is preferably removed.

The products of the Fischer-Tropsch reaction include methane, $C_{2-50}$ hydrocarbons, water and carbon dioxide, as well as unreacted syngas. Water, methane, $C_{2-17}$ hydrocarbons and carbon dioxide are substantially removed to yield a product stream including mostly $C_{18}+$ hydrocarbons. The $C_{18}+$ hydrocarbons are mostly paraffinic. The desired $C_{18-26}$ fraction can be isolated, for example, by fractional distillation. Optionally, but preferably, the fraction is hydrotreated at this stage to remove any oxygenated products.

Of course, the Fischer-Tropsch chemistry can be performed using only one set of reaction conditions, and the $C_{6-8}$ and $C_{18-26}$ fractions can be isolated from the product mixture as described above.

As discussed above, slurry reactors can be preferred for either set of Fischer-Tropsch conditions. Bubble column slurry reactors can be particularly preferred. Details regarding bubble column slurry reactors can be found, for example, in Y. T. Shah et al., Design Parameters Estimations for Bubble Column Reactors, *AIChE Journal,* 28 No. 3 pp. 353–379 (May 1982); Ramachandran et al., Bubble Column Slurry Reactor, Three-Phase Catalytic Reactors, Chapter 10, pp. 308–332 Gordon and Broch Science Publishers (1983); Deckwer et al., Modeling the Fischer-Tropsch Synthesis in the Slurry Phase, Ind. Eng. Chem. Process Des. Dev. v 21, No. 2, pp. 231–241 (1982); Kölbel et al., The Fischer-Tropsch Synthesis in the Liquid Phase, Catal. Rev.-Sci. Eng., v. 21(n), pp. 225–274 (1980); and U.S. Pat. No. 5,348,982, the contents of each of which are hereby incorporated by reference in their entirety.

Since the catalyst metal may be present in the catalyst in the form of an oxide, the catalyst may be reduced with hydrogen prior to contact with the slurry liquid. The starting slurry liquid is typically a heavy hydrocarbon with a viscosity sufficient to keep the catalyst particles suspended (typically between 4 and 100 centistokes at 100° C.). The slurry liquid also has a low enough volatility to avoid vaporization during operation (typically an initial boiling point range of between about 350° C. and 550° C.). The slurry liquid is preferably essentially free of contaminants such as sulfur, phosphorous or chlorine compounds. Initially, it may be desirable to use a synthetic hydrocarbon fluid such as a synthetic olefin oligomer as the slurry fluid.

Often, a paraffin fraction of the product having the desired viscosity and volatility is recycled as the slurry liquid. The slurry typically has a catalyst concentration of between about 2 and 40 percent catalyst, preferably between about 5 and 20 percent, and more preferably between about 7 and 15 percent catalyst based on the total weight of the catalyst, i.e., metal plus support.

Although the reactions described herein are described in terms of Fischer-Tropsch reactions, they can optionally be performed using various modifications of the literal Fischer-Tropsch process where hydrogen (or water) and carbon monoxide (or carbon dioxide) are converted to hydrocarbons (e.g., paraffins, ethers, etc.). Thus, the term Fischer-Tropsch type product or process is intended to apply to Fischer-Tropsch processes and products and the various modifications thereof and the products thereof. For example, the term is intended to apply to the Kolbel-Engelhardt process typically described by the reaction:

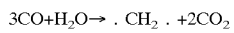

3CO+H$_2$O→ . CH$_2$ . +2CO$_2$

The Separation of Product From the Fischer-Tropsch Reaction

The products from Fischer-Tropsch reactions generally include a gaseous reaction product and a liquid reaction product. The gaseous reaction product includes hydrocarbons boiling below about 650° F. (e.g., tail gases through middle distillates). The liquid reaction product (the condensate fraction) includes hydrocarbons boiling above about 650° F. (e.g., vacuum gas oil through heavy paraffins).

The minus 650° F. product can be separated into a tail gas fraction and a condensate fraction, using, for example, a high pressure and/or lower temperature vapor-liquid separator or low pressure separators or a combination of separators. The condensate fraction includes about $C_5$ to $C_{20}$ normal paraffins and higher boiling hydrocarbons.

The fraction boiling above about 650° F. (the condensate fraction) is typically separated into a wax fraction boiling in the range of about 650° F.–1200° F. after removing particulate catalyst fines and one or more fractions boiling above about 1200° F. The wax fraction primarily contains $C_{20}$ to $C_{50}$ linear hydrocarbons (paraffins, olefins and alcohols) with relatively small amounts of higher boiling branched hydrocarbons. Typically, the separation is effected by fractional distillation. The desired $C_{6-8}$ and $C_{18-26}$ fractions can be isolated from the condensate and liquid fractions using techniques known to those of skill in the art.

Optional Process Steps

The presence of sulfur, nitrogen, halogen, selenium, phosphorus and arsenic contaminants in the feedstock is undesirable. For this reason, it is preferred to remove sulfur and other contaminants from the feed before performing the Fischer-Tropsch chemistry. Means for removing these contaminants are well known to those of skill in the art. For example, ZnO guardbeds are preferred for removing sulfur impurities. Means for removing other contaminants are well known to those of skill in the art.

In one embodiment, any methane produced by the reaction is recovered and converted to synthesis gas for recycling in the process. In some embodiments, the product stream may contain a relatively large amount of olefins that can be hydrogenated following the Fischer-Tropsch chemistry.

Removal of the methane and isolation of $C_{6-8}$ and $C_{18-26}$ fractions also provides $C_{9-17}$ and $C_{27}+$ fractions. The $C_{9-17}$ fraction is in the diesel fuel range, and can either be used directly, or alternatively, can be isomerized to improve the pour point. Methods for isomerizing hydrocarbon feeds are well known to those of skill in the art.

The $C_{27}+$ fraction can either be isolated and used directly, or can be reacted to form lower molecular weight products, as desired. For example, the high molecular weight products can be hydrocracked to provide lower molecular weight products, which can be used, for example, as components in liquid combustible fuels. The $C_{27}+$ fraction can also be converted into lube base stocks by isomerization.

Hydrocracking refers to a catalytic process, usually carried out in the presence of free hydrogen, in which the cracking of the larger hydrocarbon molecules is a primary purpose of the operation. Desulfurization and/or denitrification of the feed stock usually will also occur.

Catalysts used in carrying out hydrocracking operations are well known in the art, and it should not be necessary to describe them in detail here. See, for example, U.S. Pat. Nos. 4,347,121 and 4,810,357 for general descriptions of hydrotreating, hydrocracking, and typical catalysts used in each process. The product from the hydrocracking can be subject to distillation and/or catalytic isomerization to provide lube oils, diesel fuel, and the like.

Catalytic Reforming Processes Using the $C_{6-8}$ Product Stream

The $C_{6-8}$ product stream is reformed, for example, using catalytic reforming conditions, to form aromatic products. Reforming is a complex process and involves a number of competing processes or reaction sequences. These include dehydrogenation of cyclohexanes to aromatics, dehydroisomerization of alkylcyclopentanes to aromatics, dehydrocyclization of acyclic hydrocarbons to aromatics, and hydrocracking of paraffins to light products boiling outside the gasoline range. In addition, the dealkylation of alkylbenzenes and the isomerization of paraffins occur in reforming processes. As the $C_{6-8}$ product stream includes predominantly acyclic hydrocarbons, the major reforming reaction is dehydrocyclization.

Conditions suitable for reforming $C_{6-8}$ product streams are well known in the art, and include the AROMAX® Process and platforming or rheniforming processes. The AROMAX® Process is well known to those of skill in the art, and is described, for example, in *Petroleum & Petrochemical International*, Volume 12, No. 12, pages 65 to 68, as well as U.S. Pat. No. 4,456,527 to Buss et al., the contents of which are hereby incorporated by reference.

These processes, their commercial startup conditions, and their useful range of process operating conditions are all well known to those skilled in the art. These processes can be carried out in a single reactor or in a series of reactors.

Feedstock

The $C_{6-8}$ fraction includes normal paraffins and alpha olefins and a minimum of isoparaffins, and is used as at least a portion of the feedstock for the catalytic reforming reaction. Isoparaffins can participate in the reaction if they are not too highly branched, for example, like 2,2-dimethylbutane and 2,3-dimethylbutane. Accordingly, mono-alkylparaffins such as mono-methylparaffins can be present in the feedstock. Several di- and poly-alkylparaffins can also be present since they are relatively non-reactive under the reaction conditions. Preferably, the stream includes predominantly $C_6$ and $C_7$ hydrocarbons. Using the AROMAX® Process, yields of aromatic compounds are nearly 90% when this stream is used.

As with the Fischer-Tropsch reaction described above, the feed should be substantially free of sulfur, nitrogen, metals and other known poisons. Methods for removing such poisons from the feed have been discussed above. In a preferred embodiment, the $C_{6-8}$ hydrocarbons contacting the catalyst are substantially dry and free of sulfur, i.e., sulfur levels are preferably maintained below about 50 ppb, preferably below about 25 ppb, and more preferably below about 10 ppb. Sulfur removal systems are well known in the ultra-low sulfur reforming art. If the product of the Fischer-Tropsch reaction in the $C_{6-8}$ range is combined with other feedstocks in that range, sulfur and other impurities need to be removed.

Conversion Processes

The catalytic reforming process is a low sulfur reforming process, preferably using a bound, halided Pt L-zeolite catalyst. Catalytic reforming is well known. For example, it is described in the book, Catalytic Reforming, by D. M. Little, PennWell Books (1985), which is incorporated herein by reference in its entirety.

The reaction is preferably conducted at a temperature between 400° F. and 1100° F., more preferably between 800° F. and 1050° F. In the temperature range of from 400° C. to 600° C., the catalytic reforming reaction can occur with acceptable speed and selectivity. When using traditional reforming catalysts, if the operating temperature is below 400° C., the reaction speed is insufficient and consequently the yield is too low for industrial purposes. When the operating temperature is above 600° C., interfering secondary reactions such as hydrocracking and coking may occur, reducing the yield. These secondary reactions are minimized using the bound, halided, zeolite catalysts described herein. They can also be minimized by incorporating an alkali metal, such as potassium, or an alkaline earth metal, such as barium, strontium or calcium, preferably barium, into the catalysts. The metals can be incorporated, for example, via ion exchange, as described, for example, in U.S. Pat. No. 4,447,316 to Buss et al., the contents of which are hereby incorporated by reference.

The pressure is preferably between 0 and 400 psig, more preferably between 15 and 150 psig. The recycle hydrogen rate is sufficient to yield a hydrogen to hydrocarbon mole ratio for the feed to the reforming reaction zone between 0.1 and 20, more preferably between 0.5 and 10, and most preferably between 2 and 6. The liquid hourly space velocity (LHSV) for the hydrocarbon feed over the reforming catalyst is between 0.1 and 10 $hr^{-1}$, more preferably between 0.5 and 5 $hr^{-1}$. Reforming produces hydrogen. Thus, additional hydrogen is not needed except when the catalyst is reduced upon startup, and when the feed is first introduced. Once reforming is underway, part of the hydrogen that is produced is preferably recycled over the catalyst.

In one embodiment, aromatics are prepared by first preparing a halided zeolite catalyst, bringing the catalyst on stream using commercial startup conditions, and contacting the catalyst with the $C_{6-8}$ paraffinic fraction at catalytic reforming conditions to produce aromatics. The catalyst is preferably prepared by washing a calcined, bound zeolite catalyst base with an aqueous liquid, and adding at least one halogen-containing compound and a Group VIII metal compound to the washed base.

In a preferred embodiment, the $C_{6-8}$ fraction is converted to an aromatic product stream by catalytic conversion of the $C_{6-8}$ feed under conversion conditions that include a commercial-type catalyst startup (at a low gas flow rate and a slow heat-up rate). The process preferably uses a bound and washed halided zeolite catalyst containing a Group VIII metal, where the halided catalyst has a cycle length of >1200 hr following startup. The halided catalyst is preferably prepared by a process that involves washing a bound zeolite catalyst base or catalyst before halide addition and before reduction.

The feed can be contacted with the catalyst in a fixed bed system, a moving bed system, a fluidized system, or a batch system. Either a fixed bed system or a moving bed system is preferred. In a fixed bed system, the preheated feed is passed into at least one reactor that contains a fixed bed of the catalyst. The flow of the feed can be upward, downward or radial. The effluent from the catalytic reforming reaction zone can be separated into the desired streams or fractions.

Catalyst Selection

The catalysts used in the AROMAX® Process or similar catalytic reforming processes are preferably bound and include a Group VIII metal, preferably Pt. The catalysts are also preferably halided, and, more preferably, are (water) washed, bound, halided catalysts. The term "catalyst" includes both the final catalyst as well as precursors of the final catalyst. Precursors of the final catalyst include, for example, the calcined form of the catalyst containing the catalytic metal and also the catalyst prior to activation by reduction. As used herein, the term "bound" is intended to describe a zeolite, binder combination that is formed into aggregates such as pellets, pills, extrudates and the like. The term "catalyst base", as used herein, refers to a bound zeolite.

Zeolites

Catalysts useful in the reforming reaction typically include one or more zeolites or non-zeolitic molecular sieves and at least one catalytic metal, preferably a Group VIII metal. The catalysts typically also include a binder such as a refractory oxide, e.g., silica, alumina, chlorided alumina or silica-alumina. Preferred zeolites and/or molecular sieves are selected from those of the large and intermediate pore variety. The AROMAX® Process traditionally uses PtBaK/L-zeolite as a catalyst. Traditional platforming and rheniforming processes use $Pt/Al_2O_3$ or $PtRe/Al_2O_3$ as the catalyst. These and other catalysts and suitable reforming conditions are described, for example, in U.S. Pat. Nos. 3,546,102; 3,574,092; 3,679,575; 4,018,711; 4,104,320; 4,347,394; 4,370,224; 4,417,083; 4,434,311; 4,447,316 and 5,559,068.

Catalysts including platinum on chlorinated-alumina supports, and Pt-X on alumina or chlorinated-alumina supports, where X is rhenium, iridium or tin have been used in catalytic reforming reactions. U.S. Pat. No. 4,370,224 discloses a multi-metallic reforming catalyst that includes platinum, iridium, copper, selenium and halogen, composited with an inorganic oxide support or carrier, preferably alumina. Zeolite-containing reforming catalysts, for example, the zeolite mordenite, ZSM-type zeolites, zeolite L, Faujasites X and Y, and the zeolite omega have been used.

Representative of the large pore zeolites are ZSM-3, ZSM4, ZSM-10, ZSM-12, ZSM-20, zeolite beta, zeolite omega, zeolite L, zeolite X, zeolite Y, REY, USY, RE-USY, mordenite, LZ-210, LZ-210-M, LZ-210-T, LZ-210-A, SSZ-24, SSZ-26, SSZ-31, SSZ-33, SSZ-35, SSZ-37, SSZ41, SSZ42, SSZ-44 and MCM-58. ZSM-3 is described in U.S. Pat. No. 3,415,736. ZSM-4 is described in UK Application No. 1,117,568. ZSM-10 is described in U.S. Pat. No. 3,692,470. ZSM-12 is described in U.S. Pat. No. 3,832,449. ZSM-20 is described in U.S. Pat. No. 3,972,983. Zeolite beta is described in U.S. Pat. No. Re. 28,341 (of original U.S. Pat. No. 3,308,069). Zeolite omega is described in U.S. Pat. No. 4,241,036. Zeolite L is described in U.S. Pat. No. 3,216,789. Zeolite X is described in U.S. Pat. No. 2,882,244. Zeolite Y is described in U.S. Pat. No. 3,130,007. LZ-210, LZ-210-M, LZ-210-T, LZ-210-A and mixtures thereof are described in U.S. Pat. No. 4,534,853. SSZ-24 is described in U.S. Pat. No. 4,834,977. SSZ-26 is described in U.S. Pat. No. 4,910,006. SSZ-31 is described in U.S. Pat. No. 5,106,801. SSZ-33 is described in U.S. Pat. No. 4,963,337. SSZ-35 is described in U.S. Pat. No. 5,316,753. SSZ-37 is described in U.S. Pat. No. 5,254,514. SSZ-41 is described in U.S. Pat. No. 5,591,421. SSZ-42 is described in U.S. Ser. No. 08/199,040. SSZ-44 is described in U.S. Pat. No. 5,580,540. MCM-58 is described in U.S. Pat. No. 5,437,855. The entire contents of all these patents and patent applications are incorporated herein by reference.

Preferably, the catalyst is a n L-zeolite or a zeolite having an L-zeolite-type channel structure and size, such as ECR-2 which is described in U.S. Pat. No. 4,552,731, and ECR-31 which is described in U.S. Pat. No. 5,624,657 (Vaughan). Preferably, the catalyst is a monofunctional, non-acidic K L-zeolite. Acidity in the L-zeolite generally leads to poor performance in catalytic reforming. Examples of useful L-zeolites include those described in U.S. Pat. Nos. 3,216,789 (Breck), 4,552,731 (Vaughan), 4,544,539 (Wortel), 5,491,119 (Verduijn), and 4,530,824 (assigned to Tosoh Ltd.). The entire contents of all these patents are incorporated herein by reference. One useful non-acidic L-zeolite is manufactured by Union Oil Product (UOP), Mobile, Ala. A preferred non-acidic L-zeolite is manufactured by Tosoh Ltd., Japan, and sold under the name HSZ-500KOA. For these non-acidic zeolites, potassium is a preferred cation; a preferred catalyst comprises K L-zeolite.

Preferred catalysts are monofunctional. They do not have the acid function of conventional reforming catalysts. In contrast, conventional reforming catalysts are bifunctional, with an acid and a metal function. Examples of monofunctional catalysts include platinum on L-zeolite, wherein the L-zeolite has been exchanged with an alkali metal, as disclosed in U.S. Pat. No. 4,104,320 to Bernard et al.; platinum on L-zeolite, wherein the L-zeolite has been exchanged with an alkaline earth metal, as disclosed in U.S. Pat. No. 4,634,518 to Buss and Hughes; and platinum on L-zeolite as disclosed in U.S. Pat. No. 4,456,527 to Buss, Field and Robinson. The entire contents of all these patents are incorporated herein by reference.

The term "non-acidic" is understood by those skilled in this area of art, particularly by the contrast between monofunctional (non-acidic) reforming catalysts and bifunctional (acidic) reforming catalysts. One method of achieving non-acidity is by replacing protons with alkali and/or alkaline earth metals in the zeolite. This is preferably achieved, along with other catalyst enhancements, by an ion exchange process on the synthesized zeolite.

The composition of type L-zeolite expressed in terms of mole ratios of oxides, may be represented by the following formula:

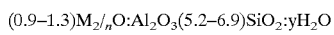

$$(0.9-1.3)M_{2/n}O:Al_2O_3(5.2-6.9)SiO_2:yH_2O$$

In the above formula, M represents a cation, n represents the valence of M, and y may be any value from 0 to about 9. Zeolite L, its X-ray diffraction pattern, its properties, and method for its preparation are described in detail in, for example, U.S. Pat. No. 3,216,789, the contents of which is hereby incorporated by reference. The actual formula may vary without changing the crystalline structure. For example, the mole ratio of silicon to aluminum (Si/Al) may vary from 1.0 to 3.5.

As discussed above, one preferred embodiment of the invention uses monofunctional Pt L-zeolite catalysts that have been treated with halogen-containing compounds. This type of halogen treatment is known. For example, U.S. Pat. No. 5,091,351 to Murakawa et al. discloses preparing a Pt L-zeolite catalyst, and then treating it with a halogen-containing compound. Other related patents that disclose halided L-zeolite catalysts include EP 498,182A or U.S. Pat. No. 5,354,933, which discloses co-impregnation of an L-zeolite with $NH_4Cl$ and $NH_4F$; U.S. Pat. Nos. 4,681,865, 4,761,512 and 5,073,652 to Katsuno et al. These patents are all incorporated herein by reference. One preferred hiz-cat for catalytic reforming comprises halided platinum K L-zeolite catalyst, especially one containing both chloride and fluoride.

Examples of useful intermediate pore size zeolites include ZSM-5, ZSM-11, ZSM-22, ZSM-23, ZSM-35, ZSM48, ZSM-57, SUZ4, SSZ-23; SSZ-25, SSZ-28, SSZ-32 and SSZ-36. ZSM-5 is described in U.S. Pat. No. Re. 29,948 (of original U.S. Pat. No. 3,702,886). ZSM-11 is described in U.S. Pat. No. 3,709,979. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is described in U.S. Pat. No. 4,585,747. SUZ-4 is described in EP Application No. 353,915. SSZ-23 is described in U.S. Pat. No. 4,859,422. SSZ-25 is described in U.S. Pat. Nos. 4,827,667 and 5,202,014. SSZ-28 is described in U.S. Pat. No. 5,200,377. SSZ-32 is described in U.S. Pat. No. 5,053,373. SSZ-36 is described in U.S. Ser. No. 60/034,252. The entire contents of all these patents and patent applications are incorporated herein by reference.

In addition to silicon, the useful zeolites herein can contain one or more framework elements other than, or in addition to, aluminum, e.g., the borosilicate zeolites. Also, the zeolites can be modified to alter their as-synthesized framework silica to alumina ratio.

Suitable catalysts can also include non-zeolitic molecular sieves with intermediate or large size pores. Non-zeolitic molecular sieves are microporous compositions that are formed from $[AlO_2]$ and $[PO_2]$ tetrahedra and have electrovalently neutral frameworks. See U.S. Pat. No. 4,861,743. Also included among the useful zeolites are materials of similar structure or behavior, e.g., crystalline metallophosphates such as those described in U.S. Pat. No. 4,440,871. Non-zeolitic molecular sieves include aluminophosphates (AlPO$_4$) as described for example in U.S. Pat. No. 4,310,440, metalloaluminophosphates as described in U.S. Pat. Nos. 4,500,651; 4,567,029; 4,544,143; and 4,686,093, and non-metal substituted aluminophosphates as described in U.S. Pat. No. 4,973,785.

Useful catalysts also include intermediate pore silicoaluminophosphates (SAPO's) as the non-zeolitic molecular sieve component. Intermediate pore SAPO's include SAPO-11, SAPO-31, SAPO41 and SM-3. U.S. Pat. No. 4,440,871 describes SAPO's generally and SAPO-11, SAPO-31 and SAPO41 specifically. The preparation of SM-3 and its unique characteristics are described in U.S. Pat. No. 5,158,665. All these patents are incorporated herein by reference.

Binders

The zeolites and/or molecular sieves are bound. They are preferably composited with matrix materials resistant to the temperatures and other conditions employed in hydrocarbon conversion processes. Such matrix materials can include active and inactive materials. Frequently, binders, such as naturally occurring clays and inorganic oxides, are added to improve the crush strength of the catalyst. The selection of binders and binding conditions depends on the zeolite and its intended use.

Suitable binder materials include synthetic or naturally occurring zeolites, alumina, clays such as montmorillonite and kaolin, and the refractory oxides of metals of Groups IVA and IVB of the Periodic Table of the Elements. Particularly useful are the oxides of silicon, titanium and zirconium, with silica being preferred, especially low acidity silica. Combinations of such oxides with other oxides are also useful, for example, silica-alumina, silica-magnesia, silica-zirconia, silica-thoria, silica-beryllia, silica-titania, titania-zirconia, silica-alumina-thoria, silica-alumina-zirconia, silica-alumina-magnesia and silica-magnesia-zirconia. These oxides can be crystalline or amorphous, or can be in the form of gelatinous precipitates, colloids, sols, or gels. Silica in the form of a silica sol is a preferred binder. A preferred silica sol has about 30 wt. % silica and contains small particles (7–9 nm in diameter), which result in catalysts with good attrition resistance and excellent crush strengths.

Extrusion aids and viscosity modifiers are generally used in addition to the binders for forming pellets or extrudates from zeolites and/or molecular sieves. These additives are typically organic compounds such as cellulose based materials, for example, Methocel® sold by Dow Chemical Co., ethylene glycol, and stearic acid. Many such compounds are known in the art. These additives should not leave a detrimental residue, i.e., one with undesirable reactivity or one that can block pores, after calcination. Preferably, the residues do not add significant amounts of alkali or alkaline earth ash to the catalyst. The above-described washing will remove low levels of these materials. The residue from the extrusion aid is preferably less than a few tenths of a percent by weight, more preferably less than 0.1 wt. %.

Methods for preparing catalyst compositions are well known to those skilled in the art and include such conventional techniques as spray drying, pelletizing, extrusion, various sphere-making techniques and the like. The methods of in-extrudate formation of the zeolite/binder described in U.S. Pat. No. 5,558,851 to Miller and in U.S. Pat. No. 5,514,362 can also be used. The entire contents of these patents are incorporated herein by reference.

The relative proportions of zeolite to the binder/matrix can vary widely. Generally, the zeolite content ranges from between about 1 to about 99 wt. %, and more usually in the range of from about 5 to about 95 wt. %, of the dry composite, more typically 50–85 wt. %.

Preferably, whole extrudates rather than crushed extrudates or unbound zeolites are used. Bound zeolites reduce the pressure drop through a reactor, provide improved flow rates, and are easier to load and unload. However, the diffusion characteristics of whole extrudates are quite different from those of unbound powdered zeolites. The interaction of a diffusing gas, such as a halocarbon, is different for a powdered versus a bound zeolite. Diffusion differences would also be especially significant if the catalyst evolves materials such as gases or solids, for example during startup. Moreover, the act of binding itself—including selecting binding materials and the binding method—as well as calcining can affect catalyst performance. For example, the binder can interact with the sieve by simply blocking internal and external sites or by chemical interaction (e.g., alkali from a basic sieve like the preferred L-zeolite of the present invention and silica are known to react under thermal and hydrothermal calcination conditions). Moreover, the distribution of impregnated materials may vary considerably on zeolite powder versus bound zeolites. Thus, studies on powders alone cannot be used to predict commercial performance of bound zeolite catalysts.

Group VIII Metal

The catalyst preferably includes at least one Group VIII metal, preferably a noble metal (Pt, Pd, Rh, Ir, Ru, Os), and more preferably platinum. Group VIII metal promoters, such as tin, germanium, cobalt, nickel, and combinations thereof can also be used. Preferred amounts of metal are 0.1 to 5 wt. %, more preferably 0.1 to 3 wt. %, and most preferably 0.3 to 1.5 wt. %, based on the L-zeolite. Platinum compounds that form positively charged platinum complex ions in solution are the preferred source of platinum. Platinum tetraammine chloride and nitrate are especially preferred.

Additionally, one or more non-platinum group metals such as tin, indium and Group VIIB metals such as rhenium can be added. Examples include Pt/Sn, Pt/Pd, Pt/Ni, and Pt/Re. These metals can be readily introduced into the composite employing a variety of known and conventional techniques, e.g., ion-exchange, incipient wetness, pore fill, impregnation, etc. Care should be taken so that the Group VIII metal, e.g., platinum, is incorporated in a manner that results in excellent and uniform dispersion. The incipient wetness impregnation method is preferred.

Halides

The catalysts are preferably "hiz-cats," also referred to herein as "halided catalysts" or "halided zeolite catalysts". The term "hiz-cat" is intended to include zeolite catalysts that result from adding halogen-containing compounds to, or from halide impregnation of, zeolites, catalyst bases (i.e., bound zeolites) or zeolite catalysts (i.e., zeolites containing catalytic metal). The halides of the hiz-cats are in addition to those that may be incorporated into the catalyst from the catalytic metal source; that is, this halogen addition or impregnation is not just that associated with conventional platinum loading and impregnation, where platinum halides are often used. Nor does this halogen treatment include conventional zeolite ion exchange operations. Zeolite ion exchange sometimes uses a halide salt, such as KCl, to replace the cations in the zeolite; this ion exchange can leave small amounts of halide on the catalyst. Moreover, the term hiz-cat is not intended to include catalysts where halide is added using alkali halides (e.g., KCl) or alkaline earth halides. Added alkali is believed to be detrimental to hiz-cats performance.

The form in which the halide is present in hiz-cats is unknown, and may be as ionic halide, neutral halide, or it may be part of a compound, such as a silica halide or Pt halide. The term "halide" is used in a broad sense, and is not intended to denote the ionic state of the added halogen or of the halogen associated with the catalyst.

The halide can be chloride, fluoride, bromide, iodide, or combinations thereof. Preferably, the hiz-cat contains chloride and/or fluoride, more preferably both. Especially preferred hiz-cats can be prepared by treating the bound zeolite or bound catalyst with halocarbons such as freons or with other chlorine-containing and/or fluorine-containing compounds, e.g., by impregnation with ammonium chloride and ammonium fluoride. Preferred hiz-cats useful in this invention have high total halide after calcination (this includes all halides, e.g., both chloride and fluoride), i.e., they contain at least about 0.9 wt. % halide, preferably at least about 1.1 wt. %, and more preferably at least about 1.3 wt. % total combined halide. More than about 5 wt. % halide does not appear to provide significant advantages. When chloride and fluoride are both present, the weight ratio of Cl to F can vary. Preferably, it is between 1:10 and 10:1. More preferably, chloride and fluoride are added in a weight ratio of about 1:1.

The terms "chloride retensivity" and "retained chloride" denote the residual chloride content of the catalyst after dry-out, reduction and about 300 hr on-stream. Hiz-cats evolve chloride during these steps, especially during reduction. Thereafter, the chloride level on the catalyst remains substantially constant as the catalyst is brought on-stream and operated. After startup, some halide does continue to evolve, but very slowly. Care should be taken not to overheat the catalyst, (i.e., temperatures above about 950° F.) since additional chloride will evolve, and this overheating is not desirable.

Bound hiz-cat performance can be significantly improved by washing, for example, with water, before the halide is added. Preferred catalysts retain less of the added chloride than poor catalysts, even though the retained chloride, i.e., the "chloride retensivity" is independent of startup conditions. The sodium content of preferred catalysts is about 0.4 wt. %. Preferred catalysts include less than about 0.5 wt. %, more preferably less than 0.45 wt. %, and most preferably less than 0.4 wt. % chloride.

Hiz-Cat Preparation

Hiz-cats can be prepared by extruding and then washing either the bound catalyst or the catalyst base before halide addition. Preferably, the catalyst is prepared by:

(a) preparing a calcined silica-bound zeolite catalyst base;
(b) washing the bound zeolite catalyst base with an aqueous liquid; and
(c) incorporating a group VIII metal and halogen-containing compound(s) comprising chlorine and fluorine into the washed base to produce a halided zeolite catalyst.

Preferably, the catalyst is prepared using a low alkali, e.g., low sodium, extrusion aid in step (a). The Pt and halogen-containing compounds can be incorporated sequentially or, preferably, simultaneously. A calcined catalyst base is preferably washed before adding the halogen-containing compounds and the Group VIII metal, e.g., platinum. In this way, these added components are not washed out of the catalyst.

The catalyst base is preferably washed with one or more volumes of wash water. The washing desirably removes at least 20%, preferably at least 50%, of the readily removable alkali.

Catalyst performance can also be improved by various ion exchange processes. Cation exchange, such as with potassium and the like, often includes a wash step. Hiz-cat performance is improved when the ion exchange includes a wash step.

Isolation of Aromatic Products

Benzene, toluene and $C_8$ aromatic streams (i.e., xylenes and ethylbenzene) can be recovered using conventional techniques such as distillation and extraction.

Alkylation of the Aromatic Products

The alkylation of aromatics, as described herein, involves reaction of olefins with aromatic rings in the presence of an acid catalyst. The reaction is similar to Friedel-Crafts alkylation chemistry, except that an olefin, rather than a haloalkane, is used to alkylate the aromatic rings. While $C_{18-26}$ is the preferred range of alkyl groups for the alkylation reaction, in some embodiments, it may be desired to prepare other alkylbenzenes where the alkyl groups have different molecular weight ranges, for example, $C_{9-17}$ or $C_{27-50}$. The processes described herein are also intended to include these embodiments.

The feedstock for the alkylation reaction as described herein is the $C_{18-26}$ fraction isolated from a Fischer-Tropsch reaction, which is mostly paraffinic. If there are significant sulfur or solid impurities, these should be removed. Moderate amounts of linear olefins (<40 mol. %) can be tolerated, as well as linear alcohols (<40 mol. %). Both of these are capable of alkylating an aromatic ring.

The paraffinic $C_{18-26}$ fraction must be converted into olefins, for example, via dehydrogenation chemistry.

Catalysts and conditions for the dehydrogenation of alkanes to form olefins are well known to those of skill in the art and are described, for example, in U.S. Pat. No. 3,445,541 to Heckelsberg et al., U.S. Pat. No. 3,856,876 to Burnett, U.S. Pat. No. 4,148,833 to Antos, U.S. Pat. No. 4,420,649 to Antos, U.S. Pat. No. 4,476,344 to Kimble, U.S. Pat. No. 4,827,066 to Herber et al., U.S. Pat. No. 4,482,646 to Eastman, U.S. Pat. No. 4,686,316 to Morrison, U.S. Pat. No. 4,7516,342 to Kimble, U.S. Pat. No. 4,777,319 to Kung, U.S. Pat. No. 4,778,942 to Vora et al., U.S. Pat. No. 4,798,911 to Lentz et al., U.S. Pat. No. 4,827,066 to Herber et al., U.S. Pat. No. 4,827,072 to Imai et al., U.S. Pat. No. 4,880,764 to Imai et al., U.S. Pat. No. 4,897,253 to Jenkins, U.S. Pat. No. 4,929,792 to Dessau, U.S. Pat. No. 4,956,517 to Johnson et al., U.S. Pat. No. 4,973,779 to Imai et al., U.S. Pat. No. 4,982,047 to Barri et al., U.S. Pat. No. 5,012,027 to Abrevaya et al., U.S. Pat. No. 5,143,886 to Iezzi et al., U.S. Pat. No. 5,308,822 to Iezzi et al., U.S. Pat. No. 5,321,192 to Cottrell et al., U.S. Pat. No. 5,430,220 to Khare et al., U.S. Pat. No. 5,563,314 to Agaskar et al., U.S. Pat. No. 5,633,421 to Iezzi et al., U.S. Pat. No. 5,905,180 to Yokoyama et al., U.S. Pat. No. 5,972,203 to Smith et al., European Pat. Application 0 558 148 A1, and European Pat. Application 0 560 437 A1, the contents of each of which are hereby incorporated by reference.

Suitable dehydrogenation catalysts typically include a Group VIII metal from the Periodic Table of the Elements, which includes iron, cobalt, nickel, palladium, platinum, rhodium, ruthenium, osmium and iridium.

Platinum and palladium or the compounds thereof are preferred for use as dehydrogenation catalysts, with platinum and compounds thereof being especially preferred. When referring to a particular metal in this disclosure as being useful, the metal may be present as an elemental metal or as a compound of the metal. Reference to a particular metal is not intended to limit the invention to any particular form of the metal unless the specific name of the compound is given, as in the examples in which specific compounds are named as being used in the preparations.

The process conditions selected for carrying out the dehydrogenation step will depend upon the dehydrogenation catalyst used. In general, the pressure is usually the lowest pressure consistent with the maintenance of catalyst stability. The pressure is typically in the range of between about 0.1 and 10 atm, preferably between about 0.5 and 3 atm. The temperature is typically between about 700° C. to about 1200° F., with temperatures in the range of between 800° F. and 950° F. being particularly preferred. The LHSV is typically between 1 and 40 $hr^{-1}$, preferably between about 25 and 35 $hr^{-1}$. In the event the catalyst deactivates with the time-on-stream, specific processes that are well known to those skilled in art are available for the regeneration of the catalysts. Any number of reactors for the dehydrogenation and alkylation steps can be used, such as fixed bed, fluidized bed, ebulated bed, and the like.

The dehydrogenation and alkylation reactions can occur in the same reactor, since the presence of aromatics is not detrimental to the dehydrogenation reaction. In this embodiment, the aromatic fraction and the $C_{18-26}$ fraction are combined in a single reactor that includes a dehydrogenation catalyst and an alkylation catalyst. However, the product of the reaction may include alkyl chains with more than one aromatic ring, resulting from dehydrogenation and alkylation of the alkyl chain on the alkylbenzenes. For this reason, it can be preferred to perform the dehydrogenation and alkylation reactions in separate reactors, and, optionally, to remove any di-olefins from the olefin stream used in the alkylation step.

The UOP Pacol and Detal processes are well-known process for alkylating aromatics using a dehydrogenation catalyst (Pacol) and an alkylation catalyst (Detal). These processes are described, for example, in Vora et al., *Chemistry and Industry*, 187–191 (1990), the contents of which are hereby incorporated by reference. In the Pacol process, the conversion of n-paraffins to mono-olefins is near equilibrium. A relatively small amount of the n-paraffins is converted to di-olefins and aromatics. In the alkylation step, diolefins produce di-phenylalkanes or heavier polymers, which tends to lower the overall product yield. However, the amount of diolefins can be minimized, for example, using the UOP DeFine process. The DeFine process is a selective hydrogenation process that converts di-olefins to mono-olefins.

In a preferred embodiment, alkyl groups are subjected to dehydrogenation conditions to form a product stream containing a mixture of unconverted n-paraffins, mono-olefins and di-olefins. The product stream is reacted with a selective catalyst to hydrogenate the di-olefins to mono-olefins. The unconverted n-paraffins and mono-olefins are sent to a separate reactor along with the aromatics. The preferred ratio of aromatics to olefins is between about 2 and 50, preferably between 5 and 20. An alkylation catalyst, typically a strong acid catalyst such as HF, sulfuric acid, an acidic ionic liquid such as a quaternary amine-chloroaluminate salt, or an acidic zeolite catalyst, is used to alkylate the aromatics. An example of an alkylation reaction is the UOP Detal process.

Typically, the reaction products include unconverted paraffins, unconverted aromatics, alkylbenzenes, heavy alkylate (aromatics with more than one alkyl group) and polymers (formed from the acid-catalyzed polymerization of olefins). The aromatics and unconverted paraffins can be obtained via fractional distillation and recycled. The product can be separated from the heavy alkylate via fractional distillation.

Additional details on the UOP Pacol, De Fine and Detal processes are described, for example, in Schultz et al., "LAB Production, Second World Conference on Detergents", Montreux, Switzerland, Oct. 5–19, 1986; "Handbook of Petroleum Refining Processes," ed. R. Myers, New York, McGraw-Hill, 1986; Vora et al., "Production of biodegradable detergent intermediates," Second World Surfactants Congress, Paris, France, May 24–27 (1988); and Broughton, "Adsorptive separations—liquids" in "Kirk-Othmer Encyclopedia of Chemical Technology," Vol. 1, 3rd ed., New York, John Wiley & Sons, 1978, the contents of which are hereby incorporated by reference. Additional examples of alkylation chemistry are described, for example, in EPA 0 731 072 by Chevron Chemical SA.

The resulting alkylbenzenes can be used directly, for example, as synthetic lubricants (synlubes) and/or detergents in a variety of applications, for example, as lubricant oils. Alternatively, they can be sulfonated to form surfactants, or hydrogenated to form alkylcyclohexanes, which are useful in synthetic lube oil compositions.

Hydrogenation of Alkylbenzenes to form Alkylcyclohexanes

Conditions for hydrogenating benzene rings to form cyclohexane rings are well known to those of skill in the art. Care must be taken to avoid hydrocracking conditions, which might strip the alkyl groups from the ring.

Suitable catalysts and conditions for hydrogenating aromatic rings without removing the alkyl side chains are well known in the art. Typical catalysts are palladium or platinum catalysts on alumina or silica/alumina supports, although ruthenium and rhodium catalysts can also be used. The reactions are typically performed at a temperature between about 200° F. and 500° F., preferably around 300° F., under a hydrogen atmosphere at a pressure of between about 100 and 500 psig.

Sulfonation of Alkylbenzenes to Form Sulfonated Alkylbenzenes

Conditions for sulfonating alkylbenzenes are well known to those of skill in the art and are described, for example, in EPA 0 731 072 by Chevron Chemical SA, the contents of which are hereby incorporated by reference. In EPA 0 731 072, alkylbenzenes are sulfonated by first forming sulfuric anhydride, and then reacting the alkylbenzene with the sulfuric anhydride. Sulfuric anhydride is formed by oxidizing sulfur dioxide at 450° C. in the presence of a vanadium oxide catalyst. The sulfonation reaction takes place in a tube maintained at 65° C. by falling film, where the sulfuric anhydride is diluted with nitrogen and the alkylbenzene/sulfur dioxide ratio is maintained at about 1.05. Residual sulfuric acid is then eliminated by thermal treatment after dilution with about 10% of 100N oil, bubbling through nitrogen at the rate of about 10 l/h/kg of product and agitating at 85° C., until a lower residual sulfuric acid content is obtained (typically less than about 0.5%). The resulting sulfonated alkylbenzenes can be used, for example, as detergents and/or dispersants.

Lube Oil Compositions

The alkylcyclohexanes formed from the hydrogenation of the alkylbenzenes are useful as lube oils or as components in lube oil compositions. The lube oil compositions preferably have a kinematic viscosity of at least 3 centistokes, more preferably at least 4 centistokes, still more preferably at least 5 centistokes, and most preferably at least 6 centistokes, where the viscosity is measured at 40° C. They also have a viscosity index (a measure of the resistance of viscosity change to changes in temperature) of at least 100, preferably 140 or more, more preferably over 150, and most preferably over 160.

Another important property for the lube oil compositions is that they have a relatively high flash point for safety reasons. Preferably, the flash point is above 90° C., more preferably above 110° C., still more preferably greater than 175° C., and most preferably between 175° C. and 300° C. The following table (Table 1) shows a correlation between viscosity and flash point of preferred lubricants for use in automobiles.

TABLE 1

| Viscosity at 40° C. (cSt) | Flash Point (D93), ° C. | Flash Point (D92), ° C. |
| --- | --- | --- |
| 3.0 | 175 | 175 |
| 4.08 | 205 | 208 |
| 4.18 | 201 | 214 |
| 6.93 | 230 | 237 |
| 11.03 | 251 | 269 |

*D92 and D93 listed in the above table refer to ASTM tests for measuring flash point:
Flash Point, COC, ° C.  D 92
Flash Point, PMCC, ° C.  D 93

The lube oil can be used, for example, in automobiles. The presence of the aromatic or cyclohexane rings on the long alkyl chains gives it relatively high additive solubility (the ability to dissolve lube oil additives) and seal swell performance, relative to lube oils that do not include the aromatic or cyclohexane rings. Seal swell (the ability to adsorb in gaskets that line the lubricating system, causing them to swell slightly and make a good seal) is higher for the alkylbenzenes and alkylcyclohexanes described herein than for paraffinic lube oils that do not include these rings.

The lube oil can also be used as a blending component with other oils. This can be particularly important when a lube oil includes alkylbenzenes of alkylcyclohexanes in combination with pure paraffinic oils, where the combination provides increased additive solubility and seal swell characteristics. For example, the lube oil can be used as a blending component with polyalphaolefins, or with mineral oils to improve the viscosity and viscosity index properties of those oils, or can be combined with isomerized petroleum wax. The lube oils can also be used as workover fluids, packer fluids, coring fluids, completion fluids, and in other oil field and well-servicing applications. For example, they can be used as spotting fluids to unstick a drill pipe that has become stuck, or they can be used to replace part or all of the expensive polyalphaolefin lubricating additives in downhole applications. Additionally, they can also be used in drilling fluid formulations where shale-swelling inhibition is important, such as those described in U.S. Pat. No. 4,941,981 to Perricone et al.

Optional Components

The lube oil compositions include the alkylcyclohexanes, optionally include conventional lubricants, and preferably also include various additives, such as lubricants, emulsifiers, wetting agents, densifiers, fluid-loss additives, viscosity modifiers, corrosion inhibitors, oxidation inhibitors, friction modifiers, demulsifiers, anti-wear agents, dispersants, anti-foaming agents, pour point depressants, detergents, rust inhibitors and the like. Other hydrocarbons, such as those described in U.S. Pat. No. 5,096,883 and/or U.S. Pat. No. 5,189,012, may be blended with the lube oil provided that the final blend has the necessary pour point, kinematic viscosity, flash point, and toxicity properties. The total amount of additives is preferably between 1–30 percent. All percentages listed herein are weight percentages unless otherwise stated.

Examples of suitable lubricants include polyol esters of $C_{12}$–$C_{28}$ acids.

Examples of viscosity modifying agents include polymers such as ethylene alpha-olefin copolymers which generally have weight average molecular weights of from about 10,000 to 1,000,000 as determined by gel permeation chromatography.

Examples of suitable corrosion inhibitors include phosphosulfurized hydrocarbons and the products obtained by reacting a phosphosulfurized hydrocarbon with an alkaline earth metal oxide or hydroxide.

Examples of oxidation inhibitors include antioxidants such as alkaline earth metal salts of alkylphenol thioesters having preferably $C_5$–$C_{12}$ alkyl side chain such as calcium nonylphenol sulfide, barium t-octylphenol sulfide, dioctylphenylamine, as well as sulfurized or phosphosulfurized hydrocarbons. Additional examples include oil soluble antioxidant copper compounds such as copper salts of $C_{10}$ to $C_{18}$ oil soluble fatty acids.

Examples of friction modifiers include fatty acid esters and amides, glycerol esters of dimerized fatty acids and succinate esters or metal salts thereof.

Dispersants are well known in the lubricating oil field and include high molecular weight alkyl succinimides being the reaction products of oil soluble polyisobutylene succinic anhydride with ethylene amines such as tetraethylene pentamine and borated salts thereof.

Pour point depressants such as $C_8$–$C_{18}$ dialkyl fumarate vinyl acetate copolymers, polymethacrylates and wax naphthalene are well known to those of skill in the art.

Examples of anti-foaming agents include polysiloxanes such as silicone oil and polydimethyl siloxane; acrylate polymers are also suitable.

Examples of anti-wear agents include zinc dialkyldithiophosphate, zinc diaryl diphosphate, and sulfurized isobutylene.

Examples of detergents and metal rust inhibitors include the metal salts of sulfonic acids, alkylphenols, sulfurized alkylphenols, alkyl salicylates, naphthenates and other oil soluble mono and dicarboxylic acids such as tetrapropyl succinic anhydride. Neutral or highly basic metal salts such as highly basic alkaline earth metal sulfonates (especially calcium and magnesium salts) are frequently used as such detergents. Also useful is nonylphenol sulfide. Similar materials made by reacting an alkylphenol with commercial sulfur dichlorides. Suitable alkylphenol sulfides can also be prepared by reacting alkylphenols with elemental sulfur. Also suitable as detergents are neutral and basic salts of phenols, generally known as phenates, wherein the phenol is generally an alkyl substituted phenolic group, where the substituent is an aliphatic hydrocarbon group having about 4 to 400 carbon atoms.

Antioxidants can be added to the lube oil to neutralize or minimize oil degradation chemistry. Examples of antioxidants include those described in U.S. Pat. No. 5,200,101, which discloses certain amine/hindered phenol, acid anhydride and thiol ester-derived products.

The combination of a metallic dithiophosphate hyperoxide decomposer and aminic antioxidant is reported to have a synergistic effect on lubricant antioxidant performance. See Maleville et al., *Lubrication Science,* V9, No. 1, pp. 3–60 (1996). Sulfur-substituted derivatives of mercapto carboxylic esters also are reported to possess antioxidant properties. See M. A. Mirozopeva et al., *Naftekhimiya,* V28, No. 6, pp. 831–837 (1988).

Additional lube oils additives are described in U.S. Pat. No. 5,898,023 to Francisco et al., the contents of which are hereby incorporated by reference.

The process will be readily understood by referring to the flow diagram in FIG. 1. In FIG. 1, a mixture of carbon monoxide and hydrogen (syngas) is added to a Fischer-Tropsch reactor (Box 10). A $C_{6-8}$ fraction and a $C_{18-26}$ fraction are separately isolated via distillation (Box 20). The $C_{6-8}$ fraction is subjected to catalytic reforming to form aromatics and hydrogen gas (Box 30) and the $C_{18-26}$ fraction is dehydrogenated to form linear alpha olefins (Box 40). The linear alpha olefins are used to alkylate the aromatics (Box 50), and the resulting alkylbenzene compounds are optionally hydrogenated to form alkylcyclohexanes (Box 60). In the flow scheme contained in FIG. 1, the process of the present invention is practiced in continuous operation. However, it is possible to practice the present invention in batch operation.

What is claimed is:

1. An integrated process for preparing alkylbenzenes, the process comprising:
    (a) subjecting syngas to Fischer-Tropsch reaction conditions in the presence of a Fischer-Tropsch catalyst to form a hydrocarbon product stream;
    (b) isolating a fraction rich in $C_{6-8}$ hydrocarbons comprising paraffins and olefins and a fraction rich in $C_{18-26}$ hydrocarbons comprising paraffins and olefins from the hydrocarbon product stream;
    (c) subjecting the fraction rich in $C_{6-8}$ hydrocarbons to catalytic reforming conditions to form $C_{6-8}$ aromatics;
    (d) optionally subjecting the fraction rich in $C_{18-26}$ hydrocarbons to dehydrogenation conditions in the presence of a dehydrogenation catalyst to form olefins; and
    (e) alkylating the $C_{6-8}$ aromatics with olefins selected from the group consisting of the olefins of step (b) contained in the fraction rich in $C_{18-26}$ hydrocarbons, the olefins of step (d), or combinations thereof, to form alkylbenzenes.

2. The process of claim 1, wherein the Fischer-Tropsch reaction conditions are such that the fraction rich in $C_{6-8}$ hydrocarbons is obtained from a reaction where the Fischer-Tropsch catalyst provides low to moderate chain growth probabilities.

3. The process of claim 2, wherein the Fischer-Tropsch catalyst comprises iron.

4. The process of claim 1, wherein the Fischer-Tropsch reaction conditions are such that the fraction rich in $C_{18-26}$ hydrocarbons is obtained from a reaction where the Fischer-Tropsch catalyst provides high chain growth probabilities.

5. The process of claim 4, wherein the Fischer-Tropsch catalyst comprises cobalt.

6. The process of claim 1, wherein the catalytic reforming step is performed using a zeolite containing catalyst.

7. The process of claim 1, wherein the catalytic reforming step is performed using platforming or rheniforming processes.

8. The process of claim 1, wherein the dehydrogenation catalyst includes at least one metal or a corresponding metal compound selected from the group consisting of iron, cobalt, nickel, ruthenium, rhodium, palladium, osmium, iridium and platinum.

9. The process of claim 1, wherein the dehydrogenation catalyst comprises a noble metal or a compound thereof.

10. The process of claim 9, wherein the noble metal is platinum or palladium or a mixture of platinum and palladium.

11. The process of claim 10, wherein the dehydrogenation catalyst also contains ruthenium or a compound of ruthenium.

12. The process of claim 1, further comprising isolating unreacted $C_{18-26}$ paraffins from the alkylation step, subjecting them to dehydrogenation conditions, and recycling them to the alkylation step.

13. The process of claim 1, wherein the alkylation reaction is performed using a solid, noncorrosive, heterogeneous catalyst.

14. The process of claim 1, further comprising combining the $C_{6-8}$ aromatics used in the alkylation step with aromatics from an additional feed.

15. The process of claim 1, further comprising combining the olefins used in the alkylation step with olefins from an additional feed.

16. An integrated process for preparing alkylcyclohexanes, the process comprising:
    (a) subjecting syngas to Fischer-Tropsch reaction conditions in the presence of a Fischer-Tropsch catalyst to form a hydrocarbon product stream;
    (b) isolating a fraction rich in $C_{6-8}$ hydrocarbons comprising paraffins and olefins and a fraction rich in $C_{18-26}$ hydrocarbons comprising paraffins and olefins from the hydrocarbon product stream;
    (c) subjecting the fraction rich in $C_{6-8}$ hydrocarbons to catalytic reforming conditions to form $C_{6-8}$ aromatics;
    (d) optionally subjecting the fraction rich in $C_{18-26}$ hydrocarbons to dehydrogenation conditions in the presence of a dehydrogenation catalyst to form olefins; and
    (e) alkylating the $C_{6-8}$ aromatics with olefins selected from the group consisting of the olefins of step (b) contained in the fraction rich in $C_{18-26}$ hydrocarbons, the olefins of step (d), or combinations thereof, to form alkylbenzenes; and
    (f) hydrogenating the alkylbenzenes to form alkylcyclohexanes.

17. The process of claim 16, wherein the Fischer-Tropsch reaction conditions are such that the fraction rich in $C_{6-8}$ hydrocarbons is obtained from a reaction where the Fischer-Tropsch catalyst provides low to moderate chain growth probabilities.

18. The process of claim 17, wherein the Fischer-Tropsch catalyst comprises iron.

19. The process of claim 16, wherein the Fischer-Tropsch reaction conditions are such that the fraction rich in $C_{18-26}$ hydrocarbons is obtained from a reaction where the Fischer-Tropsch catalyst provides high chain growth probabilities.

20. The process of claim 19, wherein the Fischer-Tropsch catalyst comprises cobalt.

21. The process of claim 16, wherein the catalytic reforming step is performed using a zeolite containing catalyst.

22. The process of claim 16, wherein the catalytic reforming step is performed using platforming or rheniforming processes.

23. The process of claim 16, wherein the dehydrogenation catalyst includes at least one metal or a corresponding metal compound selected from the group consisting of iron, cobalt, nickel, ruthenium, rhodium, palladium, osmium, iridium and platinum.

24. The process of claim 16, wherein the dehydrogenation catalyst comprises a noble metal or a compound thereof.

25. The process of claim 24, wherein the noble metal is platinum or palladium or a mixture of platinum and palladium.

26. The process of claim 25, wherein the dehydrogenation catalyst also contains ruthenium or a compound of ruthenium.

27. The process of claim 16, further comprising isolating unreacted $C_{18-26}$ paraffins from the alkylation step, subjecting them to dehydrogenation conditions, and recycling them to the alkylation step.

28. The process of claim 16, wherein the alkylation reaction is performed using a solid, noncorrosive, heterogeneous catalyst.

* * * * *